United States Patent [19]
Cantatore et al.

[11] Patent Number: 4,618,634
[45] Date of Patent: Oct. 21, 1986

[54] COMPOUNDS CONTAINING PIPERIDINE GROUPS, AS STABILIZERS FOR SYNTHETIC POLYMERS

[75] Inventors: Giuseppe Cantatore, Bitonto; Valerio Borzatta, Bologna, both of Italy

[73] Assignee: Ciba-Geigy S.p.A., Origgio, Italy

[21] Appl. No.: 706,301

[22] Filed: Feb. 27, 1985

[30] Foreign Application Priority Data

Feb. 28, 1984 [IT] Italy ................................ 19830 A/84

[51] Int. Cl.$^4$ ................. C07D 401/12; C07D 401/14; C08K 5/34; C08K 5/35
[52] U.S. Cl. ...................................... 524/97; 546/187; 546/188; 546/242; 544/130; 544/212; 544/360; 524/98; 524/99; 524/100; 524/102; 524/103
[58] Field of Search ....................... 546/188, 187, 242; 544/130, 212, 360; 524/97, 98, 99, 100, 102, 103

[56] References Cited

U.S. PATENT DOCUMENTS 4,369,321  1/1983  Cantatore ............................. 546/187

*Primary Examiner*—Robert T. Bond
*Attorney, Agent, or Firm*—Wenderoth, Lind & Ponack

[57] ABSTRACT

Novel compounds containing piperidine groups, of the general formula

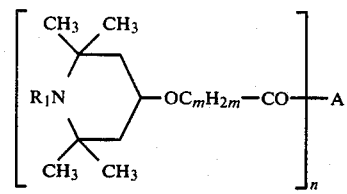

in which $R_1$ is hydrogen, O—, cyanomethyl, $C_1$–$C_{12}$-alkyl, $C_3$–$C_{12}$-alkenyl or -alkynyl, $C_7$–$C_{12}$-aralkyl or $C_1$–$C_{12}$-acyl, m is an integer from 1 to 12, n is an integer from 1 to 3 and A is an amine radical, are suitable as light stabilizers, heat stabilizers and oxidation stabilizers for synthetic polymers. Processes for their preparation are also described.

14 Claims, No Drawings

COMPOUNDS CONTAINING PIPERIDINE GROUPS, AS STABILIZERS FOR SYNTHETIC POLYMERS

The present invention relates to a novel class of compounds containing piperidine groups, which compounds can be used as light stabilisers, heat stabilisers and oxidation stabilisers for synthetic polymers.

It is known that synthetic polymers undergo a progressive change in their physical properties, like a loss of mechanical strength and colour changes, when they are exposed to sunlight or other sources of ultraviolet light. To retard the deleterious effect of sunlight on synthetic polymers, the use of various additives having light-stabilising properties has been proposed. However, the results obtained with the known stabilisers have not been fully satisfactory with all types of manufactured articles, so that a further improvement was desirable. Piperidylcarbamates with close related structure but not comparable chemically with the instant piperidyloxylakylamides are disclosed in U.S. Pat. No. 4,369,321. The present invention relates to piperidyloxyalkylamides which have shown an excellent activity as light stabilisers for synthetic polymers. The novel compounds are particularly suitable for improving the light resistance of manufactured articles of the type based on polyolefines.

In particular, the present invention relates to novel compounds of the general formula (I)

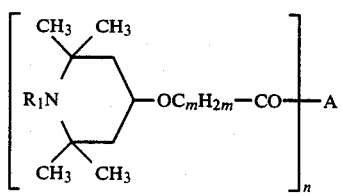

in which $R_1$ is hydrogen, O—, cyanomethyl, $C_1$-$C_{12}$-alkyl, $C_3$-$C_{12}$-alkenyl or -alkynyl, $C_7$-$C_{12}$-aralkyl or $C_1$-$C_{12}$-acyl, m is an integer from 1 to 12 and n is an integer from 1 to 3, and, if n=1, A is a radical

in which $R_2$ and $R_3$ can be identical or different and are hydrogen, $C_1$-$C_{18}$-alkyl, $C_1$-$C_{18}$-alkyl substituted by $C_1$-$C_{18}$-alkoxy or $C_2$-$C_{18}$-dialkylamino, $C_3$-$C_{18}$-alkenyl, $C_5$-$C_{18}$-cycloalkyl, $C_6$-$C_{18}$-aryl, $C_7$-$C_{18}$-aralkyl or a radical of the formula (II)

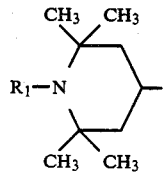

in which $R_1$ is as defined above, or A is a monovalent radical of a 5-membered to 13-membered heterocyclic compound containing at least one nitrogen atom, the free valency being on the nitrogen atom, and, with n=2, A is a radical of the formula (III), (IV) or (V)

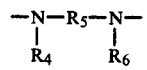

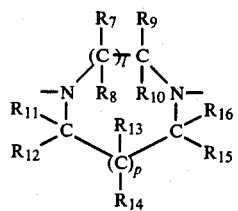

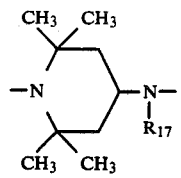

in which $R_4$, $R_6$ and $R_{17}$ can be identical or different and are as defined for $R_2$ and $R_3$, $R_5$ is $C_2$-$C_{18}$-alkylene, $C_4$-$C_{18}$-alkylene substituted by 1 to 3 oxygen atoms, $C_5$-$C_{12}$-cycloalkylene, $C_6$-$C_{12}$-arylene or $C_7$-$C_{12}$-aralkylene, the radicals $R_7$-$R_{16}$ can be identical or different and are hydrogen or methyl, $R_9$ together with $R_{10}$ and $R_{13}$ together with $R_{14}$ can be oxygen, p and 1 indipendently are zero or 1, and, with n=3, A is a radical of the formula (VI)

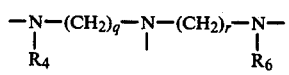

in which $R_4$ and $R_6$ are as defined above and q and r can be identical or different and are integers from 2 to 6, or A is a hexahydro-1,3,5-triazine-1,3,5-triyl radical.

Illustrative examples of the meaning of the various radicals are as follows:

for $R_1$: hydrogen, cyanomethyl, methyl, ethyl, propyl, butyl, hexyl, octyl, decyl, dodecyl, allyl, methallyl, 2-butenyl, 2-hexenyl, 10-undecenyl, propargyl, benzyl, methylbenzyl, t-butylbenzyl, hydroxybenzyl, acetyl, propionyl, butyryl, caproyl, benzoyl, acryloyl, methacryloyl and crotonyl;

for $R_2$, $R_3$, $R_4$, $R_6$ and $R_{17}$: hydrogen, methyl, ethyl, propyl, isopropyl, butyl, isobutyl, hexyl, heptyl, octyl, 2-ethylhexyl, 1,1,3,3-tetramethylbutyl, decyl, dodecyl, hexadecyl, octadecyl, 2-methoxyethyl, 2-ethoxyethyl, 3-methoxypropyl, 3-ethoxypropyl, 3-butoxypropyl, 3-octyloxypropyl, 3-dodecyloxypropyl, 3-dimethylaminopropyl, 3-diethylaminopropyl, 4-diethylaminobutyl, allyl, methallyl, 2-butenyl, 2-hexenyl, 10-undecenyl, oleyl, cyclo-hexyl, methylcyclohexyl, trimethylcyclohexyl, cyclooctyl, cyclododecyl, phenyl, methylphenyl, dimethylphenyl, tri-methylphenyl, t-butylphenyl, methoxyphenyl, ethoxyphenyl, 3,5-di-t-butyl-4-hydroxyphenyl, benzyl, methylbenzyl, hydroxybenzyl, 3,5-di-t-butyl-4-hydroxybenzyl, 2,2,6,6-tetramethylpiperidin-4-yl, 1,2,2,6,6-pentamethyl-piperidin-4-yl, 1-allyl-2,2,6,6-tetramethyl-piperidin-4-yl, 1-benzyl-2,2,6,6-tetramethyl-piperidin-4-yl and 1-acetyl-2,2,6,6-tetramethylpiperidin-4-yl;

for $R_5$: methylene, ethylene, 1,2-propylene, trimethylene, pentamethylene, hexamethylene, decamethylene, dodecamethylene, cyclohexylene, cyclohexylenedimethylene, phenylene, xylylene, 3-oxapentane-1,5-diyl, 4-oxaheptane-1,7-diyl, 4,9-dioxadodecane-1,12-diyl and 4,7,10-trioxatridecane-1,13-diyl.

For A being a monovalent radical of a heterocyclic compound, preferred examples are: pyrrolidin-1-yl, piperidin-1-yl, 2,2,6,6-tetramethyl-piperidin-1-yl, morpholin-4-yl, 4-methyl-piperazin-1-yl, 3,3,5,5-tetramethyl-piperazin-1-yl, hexahydroazepin-1-yl, azacyclotridec-1-yl or a radical of the formula

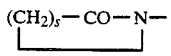

in which s is an integer from 3 to 11.

For A being a divalent radical of formula IV, preferred examples being:

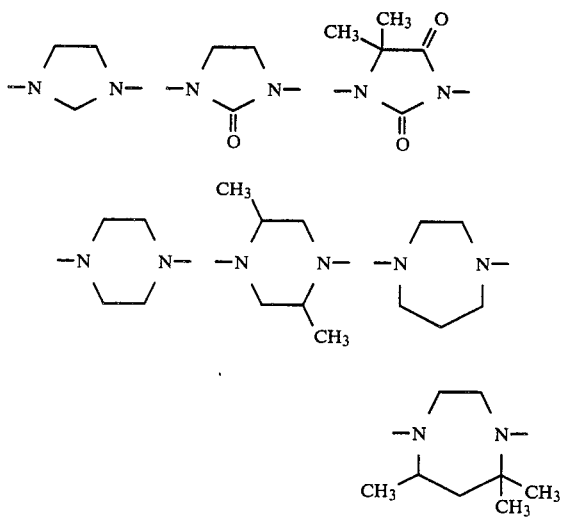

with n=3, A is preferably the hexahydro-1,3,5-triazine-1,3,5-triyl radical.

Preferred compounds of the formula (I) are those in which $R_1$ is hydrogen, methyl, allyl, benzyl or acetyl, m is 1 to 6, $R_2$, $R_3$, $R_4$, $R_6$ and $R_{17}$ are hydrogen, $C_1$–$C_{12}$-alkyl, 3-($C_1$–$C_6$-alkoxy)-propyl, $C_6$–$C_{12}$-cycloalkyl or a radical of the formula (II) in which $R_1$ is as defined above, and $R_5$ is $C_2$–$C_{12}$-alkylene or A as a heterocyclic radical is piperidin-1-yl, 2,2,6,6-tetramethylpiperidin-1-yl, hexahydroazepin-1-yl, morpholin-4-yl, piperazine-1,4-diyl or 5,5,7-trimethylhomopiperazine-1,4-diyl.

Particularly preferred compounds of the formula (I) are those in which $R_1$ is hydrogen or methyl, m is 1 or 2, $R_2$, $R_3$, $R_4$, $R_6$ and $R_{17}$ are $C_1$–$C_8$-alkyl, cyclohexyl, 2,2,6,6-tetramethyl-piperidin-4-yl or 1,2,2,6,6-pentamethyl-piperidin-4-yl and $R_5$ is $C_2$–$C_6$-alkylene or A as a heterocyclic radical is piperazine-1,4-diyl or 5,5,7-trimethylhomopierazine-1,4-diyl.

The novel compounds according to the present invention can be prepared by (a) reacting a halogenoamide of the formula (VII)

$$A-(COC_mH_{2m}X)_n \qquad (VII)$$

in which A, m and n are as defined above and X is chlorine or bromine, with an alcoholate of the formula (VIII)

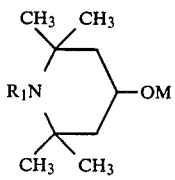

in which $R_1$ is as defined above and M is an alkali metal, the reaction being carried out in an inert organic solvent at temperatures from 0° to 200° C., preferably from 20° to 150° C., in a preferably stoichiometric molar ratio of the reactants, or (b) reacting a halogenoamide of the formula (VII) with a piperidinol of the formula (IX)

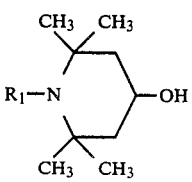

in which $R_1$ is as defined above, in an inert organic solvent at temperatures from 20° C. to 200° C., preferably from 40° to 150° C., with a preferably stoichiometric molar ratio of the reactants and in the presence of an inorganic base, such as sodium or potassium hydroxide or carbonate, and a catalyst of the formula $(R_aR_bR_cR_dY)^+Z^-$, in which $R_a$, $R_b$, $R_c$ and $R_d$ can be identical or different and are $C_1$–$C_{18}$-alkyl, $C_6$–$C_9$ aryl or $C_7$–$C_{18}$-aralkyl, Y is nitrogen or phosphorus and $Z^-$ is an anion, for example $Cl^-$, $Br^-$, $I^-$, $OH^-$ or $HSO_4^-$, or in the presence of a catalyst of the formula (X)

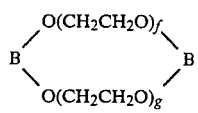

in which B is $-CH_2CH_2-$,

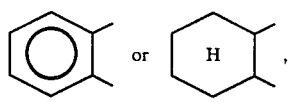

and f and g can be identical or different and are integers from 1 to 3, or in the presence of a catalyst of the formula (XI)

$$HO(CH_2CH_2O)_tH \qquad (XI)$$

in which t is an integer from 4 to 250, or in the presence of a solid inorganic base, such as sodium or potassium hydroxide, without any further organic catalyst.

As catalyst could be employed, for example tetraethylammonium bromide, tetrabuthylammonium bromide, tetrabutylammonium hydrogen sulfate, benzyltriethylammonium chloride, benzyltriethylammonium bromide, lauryldimethylbenzylammonium chloride, cetyltrimethylammonium bromide, myristyltrimethylammonium bromide, benzyltriphenylphosphonium chloride, 18-crown-6-, 15-crown-5 or usual polyethyleneglycols.

The halogenoamides of the formula (VII), which are the starting materials for the preparation of the compounds of the formula (I), can be prepared by known processes, for example by reacting a halogenoacyl halide $XCOC_mH_{2m}X$ with an amine of the formula $A-(H)_n$, in which A, X, m and n are as defined above, the reaction being carried out at a low temperature, preferably below 0° C., in a suitable solvent, for example a chlorinated hydrocarbon, with subsequent addition of NaOH in a stoichiometric quantity.

The halogenoamides can be used directly in the subsequent reaction, without isolation from the reaction mixture, or after separation and purification.

In order to illustrate the present invention more clearly, several examples of the preparation of compounds of the formula (I) are described below; these examples are given by way of illustration only and do not imply any restriction.

EXAMPLE 1

Preparation of N,N'-bis-[2-(1,2,2,6,6-pentamethyl-piperidin-4-yloxy)-acetyl]-N,N'-bis-(2,2,6,6-tetramethyl-piperidin-4-yl)-1,6-diaminohexane 38.29 g (0.07 mol) of N,N'-bis-(2-chloroacetyl)-N,N'-bis-(2,2,6,6-tetramethyl-piperidin-4-yl)-1,6-diaminohexane are dissolved in 100 ml of anhydrous xylene. The solution thus obtained is cooled to 0°–10° C.; the solution of 29.72 g (0.154 mol) of the sodium alcoholate of 1,2,2,6,6-pentamethyl-piperidin-4-ol in 120 ml of xylene (obtained beforehand by reacting 3.54 g (0.154 mol) of sodium with 26.38 g (0.154 mol) of 1,2,2,6,6-pentamethyl-piperidin-4-ol in 120 ml of anhydrous xylene) is then added slowly with continuous stirring.

During the addition, the temperature is controlled in such a way that it is maintained in the range 0°–10° C.

When the addition is complete, the mixture is left for 2 hours at room temperature with stirring and then for 8 hours at 60°–70° C. with stirring.

The solution is cooled and washed with water and then dehydrated and evaporated.

The oily residue is crystallised from n-hexane.

The product obtained melts at 116.8° C.

Analysis for $C_{48}H_{92}N_6O_4$: Calculated: C 70.54%; H 11.35%; N 10.28%; Found: C 70.64%; H 11.43%; N 10.33%.

EXAMPLES 2–13

The procedure described in Example 1 is repeated for preparing the following compounds of the formula (I)

TABLE 1

| EXAMPLE NO. | $R_1$ | m | n | A | Melting point (°C.) |
|---|---|---|---|---|---|
| 2 | H | 1 | 2 | —N—(CH₂)₆—N— (bis-2,2,6,6-tetramethylpiperidin-4-yl) | 44–45 |
| 3 | CH₃ | 1 | 2 | —N—(CH₂)₃—N— (bis-2,2,6,6-tetramethylpiperidin-4-yl) | 116–117 |
| 4 | H | 1 | 2 | —N—(CH₂)₃—N— (bis-2,2,6,6-tetramethylpiperidin-4-yl) | 95–96 |
| 5 | CH₃ | 1 | 2 | —N—(CH₂)₂—N— (bis-2,2,6,6-tetramethylpiperidin-4-yl) | 166–167 |
| 6 | H | 1 | 2 | —N—(CH₂)₂—N— (bis-2,2,6,6-tetramethylpiperidin-4-yl) | 180–181 |

TABLE 1-continued

| EXAMPLE NO. | R₁ | m | n | A | Melting point (°C.) |
|---|---|---|---|---|---|
| 7 | CH₃ | 1 | 2 | —N—(CH₂)₂—N— (each N bearing a cyclohexyl group) | 150–151 |
| 8 | H | 1 | 2 | —N—(CH₂)₂—N— (each N bearing a cyclohexyl group) | 183–184 |
| 9 | CH₃ | 2 | 2 | —N—(CH₂)₆—N— (each N bearing a 2,2,6,6-tetramethylpiperidin-4-yl group, NH) | 77–78 |
| 10 | CH₃ | 1 | 2 | —N(piperazine)N— | 180–181 |
| 11 | H | 1 | 2 | —N(piperazine)N— | 167–168 |
| 12 | CH₃ | 1 | 2 | —N(2,2,5-trimethylpiperazine)N— | 118–119 |
| 13 | H | 1 | 2 | —N(2,2,5-trimethylpiperazine)N— | 44–46 |
| 14 | CH₃ | 1 | 2 | —N(C₂H₅)—(2,2,6,6-tetramethylpiperidin-4-yl)N— | resin |

EXAMPLE 15

Preparation of
N-[2-(1,2,2,6,6-pentamethyl-piperidin-4-yloxy)-acetyl]-
N-(2,2,6,6-tetramethyl-piperidin-4-yl)-ethylamine (a)
N-(2-Chloroacetyl)-N-(2,2,6,6-tetramethyl-piperidin-4-yl)-ethylamine A solution of 23.16 g (0.205 mol) of chloroacetyl chloride in 30 ml of methylene chloride is slowly added to a solution of 36.85 g (0.2 mol) of N-(2,2,6,6-tetramethyl-piperidin-4-yl)-ethylamine in 160 ml of methylene chloride cooled to −20° C., taking care that the temperature does not rise above −10° C. The mixture is stirred for one hour and then left to stand, allowing the temperature to rise to 0° C.; a solution of 8.4 g (0.21 mol) of sodium hydroxide in 35 ml of water is then added in the course of 1 hour.

The mixture is stirred at room temperature for 1 hour, the aqueous phase is separated off, and the organic phase is evaporated to dryness.

The residue, which is 98.7% pure according to gas chromatography, can be used in the crude form or after crystallisation from n-hexane.

The crystalline product melts at 58.5° C.

Analysis for $C_{13}H_{25}ClN_2O$ Calculated: C 59.87%; H 9.66%; N 10.74%; Cl 13.59%; Found: C 59.93%; H 9.78%; N 10.70%; Cl 13.50%.

(b)

N-[2-(1,2,2,6,6-Pentamethyl-piperidin-4-yloxy)-acetyl]-N-(2,2,6,6-tetramethyl-piperidin-4-yl)-ethylamine 26.05 g (0.1 mol) of N-(2-chloroacetyl)-N-(2,2,6,6-tetramethyl-piperidin-4-yl)-ethylamine prepared as described above are dissolved in 100 ml of anhydrous xylene.

The solution thus obtained is cooled to 0°–10° C.; a solution of 21.23 g (0.11 mol) of the sodium alcoholate of 1,2,2,6,6-pentamethyl-piperidin-4-ol in xylene (obtained beforehand by reacting 2.53 g (0.11 mol) of sodium with 18.85 g (0.11 mol) of 1,2,2,6,6-pentamethyl-piperidin-4-ol in 85 ml of anhydrous xylene) is then added slowly and with stirring.

During the addition, the temperature is controlled in such a way that it remains within the range from 0°–10° C.

After the end of the addition, the mixture is left to stand for 2 hours at room temperature, with stirring, and then for 8 hours at 60°–70° C.

The mixture is cooled and washed with water. The solution is dehydrated and evaporated.

The oily residue is distilled.

The product obtained boils at 193° C./0.7 mm Hg, and the distillate crystallises, giving a melting point of 66°–67° C.

Analysis for $C_{23}H_{45}N_3O_2$: Calculated: C 69.83%; H 11.46%; N 10.62%; Found: C 70.16%; H 11.55%; N 10.70%.

EXAMPLE 16

Preparation of
N-[2-(2,2,6,6-tetramethyl-piperidine-4-yloxy)-acetyl]-N-(2,2,6,6-tetramethyl-piperidin-4-yl)-ethylamine By a procedure analogous to that described in Example 15.b, N-[2-(2,2,6,6-tetramethyl-piperidin-4-yloxy)-acetyl]-N-(2,2,6,6-tetramethyl-piperidin-4-yl)-ethylamine was prepared from 26.05 g (0.1 mol) of N-(2-chloroacetyl)-N-(2,2,6,6-tetramethyl-piperidin-4-yl)-ethylamine and 19.83 g (0.11 mol) of the sodium alcoholate of 2,2,6,6-tetramethyl-piperidin-4-ol in 85 ml of xylene.

The product obtained crystallises from n-hexane and has a melting point of 75°–76° C.

Analysis for $C_{22}H_{43}N_3O_2$: Calculated: C 69.24%; H 11.36%; N 11.01%; Found: C 68.91%; H 11.37%; N 10.97%.

EXAMPLE 17

Preparation of
N-[2-(1,2,2,6,6-pentamethyl-piperidin-4-yloxy)-acetyl]-N-(2,2,6,6-tetramethyl-piperidin-4-yl)-butylamine (a)

N-(2-Chloroacetyl)-N-(2,2,6,6-tetramethyl-piperidin-4-yl)-butylamine

By a procedure analogous to that described in Example 15.a, N-(2-chloroacetyl)-N-(2,2,6,6-tetramethyl-piperidin-4-yl)-butylamine was prepared from 23.16 g (0.205 mol) of chloroacetyl chloride and 42.48 g (0.2 mol) of N-(2,2,6,6-tetramethyl-piperidin-4-yl)-butylamine.

The product obtained distils over at 138°–139°/0.1 mm Hg.

Analysis for $C_{15}H_{29}ClN_2O$: Calculated: C 62.37%; H 10.12%; N 9.70%; Cl 12.27%; Found: C 62.45%; H 10.18%; N 9.61%; Cl 12.19%.

(b)

N-[2-(1,2,2,6,6-Pentamethyl-piperidin-4-yloxy)-acetyl]-N-(2,2,6,6-tetramethyl-piperidin-4-yl)-butylamine By a procedure analogous to that described in Example 15.b, N-[2-(1,2,2,6,6-pentamethyl-piperidin-4-yloxy)-acetyl]-N-(2,2,6,6-tetramethyl-piperidin-4-yl)-butylamine was prepared from 28.8 g (0.1 mol) of N-(2-chloroacetyl)-N-(2,2,6,6-tetramethyl-piperidin-4-yl)-butylamine and 21.23 g (0.11 mol) of the sodium alcoholate of 1,2,2,6,6-pentamethyl-piperidin-4-ol in 85 ml of xylene.

The product obtained crystallises from n-hexane and has a melting point of 71°–72° C.

Analysis for $C_{25}H_{49}N_3O_2$: Calculated: C 70.87%; H 11.66%; N 9.92%; Found: C 71.27%; H 11.67%; N 9.98%.

EXAMPLE 18

Preparation of
N-[2-(2,2,6,6-tetramethyl-piperidin-4-yloxy)-acetyl]-N-(2,2,6,6-tetramethyl-piperidin-4-yl)-butylamine By a procedure analogous to that described in Example 15.b, N-[2-(2,2,6,6-tetramethyl-piperidin-4-yloxy)-acetyl]-N-(2,2,6,6-tetramethyl-piperidin-4-yl)-butylamine was prepared from 28.8 g (0.1 mol) of N-(2-chloroacetyl)-N-(2,2,6,6-tetramethyl-piperidin-4-yl)-butylamine and 19.83 g (0.11 mol) of the sodium alcoholate of 2,2,6,6-tetramethyl-piperidin-4-ol in 85 ml of xylene.

The product obtained boils at 179°–180° C./0.5 mm Hg.

Analysis for $C_{24}H_{47}N_3O_2$: Calculated: C 70.37%; H 11.56%; N 10.26%; Found: C 70.80%; H 11.60%; N 10.35%.

EXAMPLE 19

Preparation of
N-[2-(2,2,6,6-tetramethyl-piperidin-4-yloxy)-acetyl]-N-(2,2,6,6-tetramethyl-piperidin-4-yl)-3-methoxypropylamine (a)

N-(2-Chloroacetyl)-N-(2,2,6,6-tetramethyl-piperidin-4-yl)-3-methoxypropylamine

By a procedure analogous to that described in Example 15.a, N-(2-chloroacetyl)-N-(2,2,6,6-tetramethyl-piperidin-4-yl)-3-methoxypropylamine was prepared from 23.16 g (0.205 mol) of chloroacetyl chloride and 45.68 g (0.2 mol) of N-(2,2,6,6-tetramethyl-piperidin-4-yl)-3-methoxypropylamine.

The product obtained distils over at 171°–173° C./1.1 mm Hg.

Analysis for $C_{15}H_{29}ClN_2O_2$: Calculated C 59.10%; H 9.59%; N 9.19%; Cl 11.63%; Found: C 59.05%; H 9.69%; N 9.13%; Cl 11.52%.

(b) N-[2-(2,2,6,6,-Tetramethyl-piperidin-4-xyloxy)-acetyl]-N-(2,2,6,6-tetramethyl-piperidin-4-yl)-3-methoxyproplamine By a procedure analogous to that described in Example 15.b, N-[2-(2,2,6,6-tetramethyl-piperidin-4-yloxy)-acetyl]-N-(2,2,6,6-tetramethyl-piperidin-4-yl)-3-methoxypropylamine was prepared from 30.44 g (0.1 mol) of N-(2-chloroacetyl)-N-(2,2,6,6-tetramethyl-piperidin-4-yl)-3-methoxypropylamine and 19.83 g (0.11 mol) of the sodium alcoholate of 2,2,6,6-tetramethyl-piperidin-4-ol in 85 ml of xylene.

The product obtained crystallises from n-hexane and has a melting point of 55°–56° C.

Analysis for $C_{24}H_{47}N_3O_3$: Calculated: C 67.72%; H 11.13%; N 9.87%; Found: C 67.91%; H 11.23%; N 9.84%.

EXAMPLE 20

Preparation of N-[2-(2,2,6,6-tetramethyl-piperidin-4-yloxy)-acetyl]-N-(2,2,6,6-tetramethyl-piperidin-4-yl)-n-octylamine A solution of 24.9 g (0.22 mol) of chloroacetyl chloride in 30 ml of xylene is slowly added to a solution of 53.6 g (0.2 mol) of N-(2,2,6,6-tetramethyl-piperidin-4-yl)-n-octylamine in 160 ml of xylene cooled to −10° C., taking care that the temperature does not exceed −5° C.

The mixture is stirred for 10 hours, the temperature being allowed to rise to ambient temperature.

The mixture is then cooled to 0° C. and a solution of 8.8 g (0.22 mol) of sodium hydroxide in 50 ml of water is added in the course of one hour. The mixture is stirred at ambient temperature for one hour, the aqueous phase is separated off and the organic phase is dried by azeotropic distillation and concentrated in order to obtain an anhydrous solution. According to gas chromatography, the product obtained (N-(2-chloroacetyl)-N-(2,2,6,6-tetramethyl-piperidin-4-yl)-n-octylamine) is 96.6% pure, and the product is used directly in the next reaction. The solution thus obtained is concentrated to 100 ml and cooled to 0°–10° C.

A solution of 35.8 g (0.2 mol) of the sodium alcoholate of 2,2,6,6-tetramethyl-piperidin-4-ol in 150 ml of xylene (obtained beforehand by reacting 4.6 g (0.2 mol) of sodium with 31.4 g (0.2 mol) of 2,2,6,6-tetramethyl-piperidin-4-ol in 150 ml of anhydrous xylene) is added slowly and with stirring.

During the addition, the temperature is controlled in order to maintain it in the range of 0°–10° C. After the end of the addition, the mixture is left, with stirring, for 2 hours at ambient temperature and for 8 hours at 60°–70° C. and then cooled and washed with water. The solution is dehydrated and evaporated. The oily residue is distilled.

The product distils at 185° C./0.5 mm Hg.

Analysis for $C_{28}H_{55}N_3O_2$: Calculated C 72.21%; H 11.90%; N 9.02%; Found: C 72.11%; H 11.98%; N 8.98%.

As mentioned at the outset, the compounds of the formula (I) are very effective in improving the light stability, heat stability and oxidation stability of synthetic polymers, for example high-density and low-density polyethylene, polypropylene, ethylene/propylene copolymers, ethylene/vinyl acetate copolymers, polybutadiene, polyisoprene, polystyrene, butadiene/styrene copolymers, vinyl chloride/vinylidene chloride polymers and copolymers, polyoxymethylene, polyurethanes, saturated and unsaturated polyesters, polyamides, polycarbonates, polyacrylates, alkyd resins and epoxide resins.

The compounds of the formula (I) can be mixed with the synthetic polymers in various proportions depending on the nature of the polymer, the end use and the presence of other additives. In general, it is advantageous to employ from 0.01 to 5% by weight of the compounds of the formula (I), relative to the weight of the polymers, preferably from 0.05 to 1%. The compounds of the formula (I) can be incorporated into the polymeric materials by various processes, such as dry blending in the form of powders, or wet mixing in the form of solutions or suspensions, or mixing in the form of a masterbatch; in these operations, the synthetic polymer can be employed in the form of powder, granules, a solution, a suspension or in the form of a latex.

The polymers stabilised with the products of the formula (I) can be used for the preparation of moulded articles, films, tapes, fibres, monofilaments, surface-coatings and the like.

If desired, other additives, such as antioxidants, ultraviolet absorbers, nickel stabilisers, pigments, fillers, plasticisers, antistatic agents, flameproofing agents, lubricants, anti-corrosion agents and metal deactivators, can be added to the mixtures of the compounds of the formula (I) with the synthetic polymers.

Examples of additives which can be mixed with the compounds of the formula (I) are, in particular:

Phenolic antioxidants, for example 2,6-di-t-butyl-p-cresol, 4,4′-thio-bis-(3-methyl-6-t-butylphenol), 1,1,3-tris-(2-methyl-4-hydroxy-5-t-butylphenyl)-butane, octadecyl 3-(3,5-di-t-butyl-4-hydroxyphenyl)-propionate, pentaerythritol tetrakis-3-(3,5-di-t-butyl-4-hydroxyphenyl)-propionate, tris-(3,5-di-t-butyl-4-hydroxybenzyl)isocyanurate, tris-(4-t-butyl-3-hydroxy-2,6-dimethylbenzyl)isocyanurate and calcium monoethyl 3,5-di-t-butyl-4-hydroxybenzylphosphonate;

Secondary antioxidants, such as esters of thiodipropionic acid, for example di-n-dodecyl thiodipropionate and di-n-octadecyl thiodipropionate; aliphatic sulfides and disulfides, for example di-n-dodecyl sulfide, di-n-octadecyl sulfide and di-n-octadecyl disulfide; aliphatic, aromatic or aliphatic-aromatic phosphites and thiophosphites, for example tri-n-dodecyl phosphite, tris-(nonylphenyl)phosphite, tri-n-dodecyl trithiophosphite, phenyl di-n-decyl phosphite, di-n-octadecyl pentaerythritol diphosphite, tris(2,4-di-t-butylphenyl)phosphite and tetrakis-(2,4-di-t-butylphenyl)4,4′-biphenylenediphosphonite;

Ultraviolet absorbers, for example 2-hydroxy-4-n-octyloxybenzophenone, 2-hydroxy-4-n-dodecyloxybenzophenone, 2-(2-hydroxy-3,5-di-t-butylphenol)-5-chlorobenzotriazole, 2-(2-hydroxy-3,5-di-t-amylphenyl)-benzotriazole, 2,4-di-t-butylphenyl 3,5-di-t-butyl-4-hydroxybenzoate, hexadecyl 3,5-di-t-butyl-4-hydroxybenzoate, phenyl salicylate, p-t-butylphenyl salicylate, 2-ethoxy-2′-ethyl-oxanilide, 2-ethoxy-5-t-butyl-2′-ethyl-oxanilide, 2-ethoxy-2′-ethyl-5,5′-di-t-butyl-oxanilide;

Hindered amine-type light stabilisers, for example 2,2,6,6-tetramethyl-pipieridin-4-yl benzoate, bis-(2,2,6,6-tetramethyl-piperidin-4-yl)sebacate, bis-(1,2,2,6,6-pentamethyl-piperidin-4-yl)-sebacate, bis-(1,2,2,6,6-pentamethylpiperidin-4-yl)butyl-3,5-di-t-butyl-4-hydroxybenzylmalonate, piperidinyl derivatives of triazine polymers of the type described in U.S. Pat. No. 4,086,204 and piperidine polyesters of the type described in U.S. Pat. No. 4,233,412, 2,2,4,4-tetramethyl-7-oxa-3,20-diazadispiro[5.1.11.2]heneicosan-21-one and 1,1'-ethylene-bis-(3,3,5,5-tetramethylpiperiazinone);

Light stabilisers based on nickel, for example Ni monoethyl 3,5-di-t-butyl-4-hydroxybenzyl-phosphonate, the butylamine-Ni 2,2'-thio-bis-(4-t-octylphenolate) complex, Ni 2,2'-thio-bis-(4-t-octylphenolphenolate), Ni dibutyldithiocarbamate, Ni 3,5-di-t-butyl-4-hydroxybenzoate and the Ni complex of 2-hydroxy-4-n-octyloxybenzophenone;

Organo-tin stabilisers, for example dibutyl-tin maleate, dibutyl-tin laurate and dioctyl-tin maleate;

Acrylic esters, for example ethyl $\alpha$-cyano-$\beta,\beta$-diphenylacrylate and methyl $\alpha$-cyano-$\beta$-methyl-4-methoxycinnamate;

Metal salts of higher fatty acids, for example calcium stearate, barium stearate, cadmium stearate, zinc stearate, lead stearate, nickel stearate, magnesium behenate, calcium behenate, barium behenate, zinc behenate, calcium laurate, cadmium laurate, zinc laurate and barium laurate;

Organic and inorganic pigments, for example Colour Index Pigment Yellow 37, Colour Index Pigment Yellow 83, Colour Index Pigment Red 144, Colour Index Pigment Red 48:3, Colour Index Pigment Blue 15, Colour Index Pigment Green 7, titanium dioxide, iron oxide and the like.

The efficiency, as stabilisers, of the products prepared according to the present invention is illustrated in the examples which follow, in which some products obtained in the preparation examples are used for stabilising polypropylene tapes and sheets.

EXAMPLE 21

2 g of each of the products, indicated in Table 2, 1 g of pentaerythritol tetrakis-3-(3,5-di-t-butyl-4-hydroxyphenyl)-propionate and 1 g of calcium stearate are mixed, in a powder mixer, with 1,000 g of polypropylene powder of melt index 2.4 (Propathene HF 18, a product of Imperial Chemical Industries). The mixtures obtained are extruded at a temperature of 180°–220° C., to give polymer granules which are then converted into stretched tapes of 50 μm thickness and 2.5 mm width, under the following working conditions:

extruder temperature: 220°–240° C.
head temperature: 240° C.
stretch ratio: 1:6

The tapes thus prepared are exposed, mounted on a white card, in a 65 WR model W Weather-Ometer (ASTM G 27-70), with a black panel temperature of 63° C.

The residual tenacity is measured on samples, taken after various times of exposure to light, by means of a constant-speed tensometer; the exposure time in hours ($T_{50}$) needed to halve the initial tenacity is then calculated.

For comparison, polypropylene tapes prepared under the same conditions as indicated above, but without the addition of the compounds of the invention, are exposed.

The results obtained are shown in Table 2:

TABLE 2

| Stabiliser | $T_{50}$ (hours) |
|---|---|
| none | 230 |

TABLE 2-continued

| Stabiliser | $T_{50}$ (hours) |
|---|---|
| Compound of Example 1 | 2,600 |
| Compound of Example 2 | 2,430 |
| Compound of Example 3 | 2,850 |
| Compound of Example 4 | 2,900 |
| Compound of Example 5 | 1,640 |
| Compound of Example 6 | 2,520 |
| Compound of Example 7 | 1,760 |
| Compound of Example 8 | 1,950 |
| Compound of Example 9 | 2,070 |
| Compound of Example 10 | 2,600 |
| Compound of Example 12 | 1,720 |
| Compound of Example 13 | 2,040 |
| Compound of Example 15 | 2,880 |
| Compound of Example 16 | 2,170 |
| Compound of Example 17 | 2,540 |
| Compound of Example 18 | 2,300 |
| Compound of Example 20 | 1,860 |

EXAMPLE 22

1.0 g of each of the products indicated in Table 3, 1 g of pentaerythritol tetrakis-3-(3,5-di-t-butyl-4-hydroxyphenyl)-propionate, 1 g of calcium stearate, 1 g of Filofin Blue 600 and 1,000 g of polypropylene powder of melt index 3 (Propathene HF 18, a product of Imperial Chemical Industries) are intimately mixed in a slow mixer. The mixtures obtained are extruded at a temperature of 200°–220° C. to give granules of polymer, which are then converted into 2 mm thick sheets by die extrusion at 250° C.

The sheets obtained are exposed in a 65 WR model Weather-Ometer (ASTM G 27-70), with a black panel temperature of 63° C., up to the onset of surface embrittlement (chalking).

For comparison, a polypropylene sheet prepared under the same conditions as indicated above, but without the addition of the compounds according to the invention, is exposed.

The exposure time (in hours) required for such an onset of embrittlement is indicated in Table 3.

TABLE 3

| Stabiliser | Embrittlement time (hours) |
|---|---|
| none | 500 |
| Compound of Example 2 | 2,200 |
| Compound of Example 3 | 3,480 |
| Compound of Example 4 | 2,660 |
| Compound of Example 5 | 2,480 |
| Compound of Example 6 | 2,310 |
| Compound of Example 12 | 3,230 |
| Compound of Example 15 | 3,650 |
| Compound of Example 16 | 3,770 |
| Compound of Example 17 | 3,300 |
| Compound of Example 18 | 3,770 |
| Compound of Example 20 | 3,230 |

What we claim is:

1. A compound of the formula

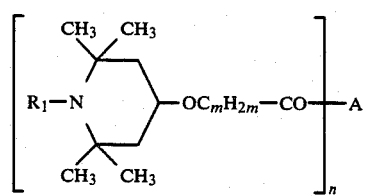

in which $R_1$ is hydrogen, O—, cyanomethyl, $C_1$-$C_{12}$-alkyl, $C_3$-$C_{12}$-alkenyl or -alkylnyl, $C_7$-$C_{12}$-aralkyl or $C_1$–$C_{12}$-acyl, m is an integer from 1 to 12 and n is an integer from 1 to 3, and, if n=1, A is a radical

in which $R_2$ and $R_3$ can be identical or different and are hydrogen, $C_1$–$C_{18}$-alkyl, $C_1$–$C_{18}$-alkyl substituted by $C_1$–$C_{18}$-alkoxy or $C_2$–$C_{18}$-dialkylamino, $C_3$–$C_{18}$-alkenyl, $C_5$–$C_{18}$-cycloalkyl, $C_6$–$C_{18}$-aryl, $C_7$–$C_{18}$-aralkyl or a radical of the formula (II)

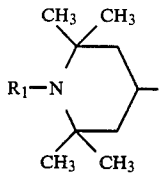 (II)

in which $R_1$ is as defined above, or A is a monovalent radical of a 5-membered to 13-membered heterocyclic compound containing at least one nitrogen atom, the free valency being on the nitrogen atom, and, with n=2, A is a radical of the formula (III), (IV) or (V)

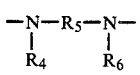 (III)

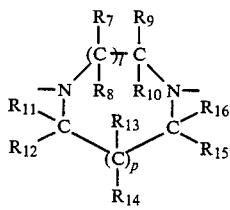 (IV)

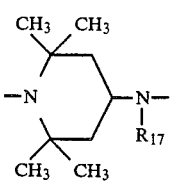 (V)

in which $R_4$, $R_6$ and $R_{17}$ can be identical or different and are as defined for $R_2$ and $R_3$, $R_5$ is $C_2$–$C_{18}$-alkylene, $C_4$–$C_{18}$-alkylene substituted by 1 to 3 oxygen atoms, $C_5$–$C_{12}$-cycloalkylene, $C_6$–$C_{12}$-arylene or $C_7$–$C_{12}$-aralkylene, the radicals $R_7$–$R_{16}$ can be identical or different and are hydrogen or methyl, $R_9$ together with $R_{10}$ and $R_{13}$ together with $R_{14}$ can be oxygen, p and l indipendently are zero or 1, and, with n=3, A is a radical of the formula (VI)

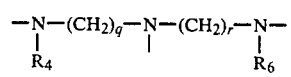 (VI)

in which $R_4$ and $R_6$ are as defined above and q and r can be identical or different and are integers from 2 to 6, or A is a hexahydro-1,3,5-triazine-1,3,5-triyl radical.

2. A compound according to claim 1 of the formula (I), in which $R_1$ is hydrogen, methyl, allyl, benzyl or acetyl, m is 1 to 6, $R_2$, $R_3$, $R_4$, $R_6$ and $R_{17}$ are hydrogen, $C_1$–$C_{12}$-alkyl, 3-($C_1$–$C_6$-alkoxy)-propyl, $C_6$–$C_{12}$-cycloalkyl or a radical of the formula (II)

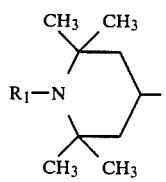 (II)

in which $R_1$ is as defined above, and $R_5$ is $C_2$–$C_{12}$-alkylene or A as a heterocyclic radical is piperidin-1-yl, 2,2,6,6-tetramethyl-piperidin-1-yl, hexahydroazepin-1-yl, morpholin-4-yl, piperazine-1,4-diyl or 5,5,7-trimethylhomopiperazine-1,4-diyl.

3. A compound according to claim 1 of the formula (I), in which $R_1$ is hydrogen or methyl, m is 1 or 2, $R_2$, $R_3$, $R_4$, $R_6$ and $R_{17}$ are $C_1$–$C_8$-alkyl, cyclohexyl, 2,2,6,6-tetramethyl-piperidin-4-yl or 1,2,2,6,6-pentamethyl-piperidin-4-yl and $R_5$ is $C_2$–$C_6$-alkylene or A as a heterocyclic radical, is piperiazine-1,4-diyl or 5,5,7-trimethylhomopiperazine-1,4-diyl.

4. The compound of the formula:

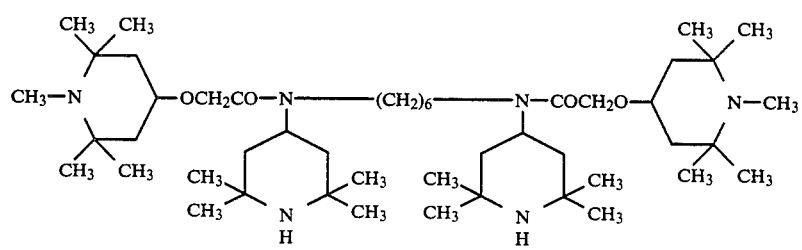

according to claim 1.

5. The compound of the formula:

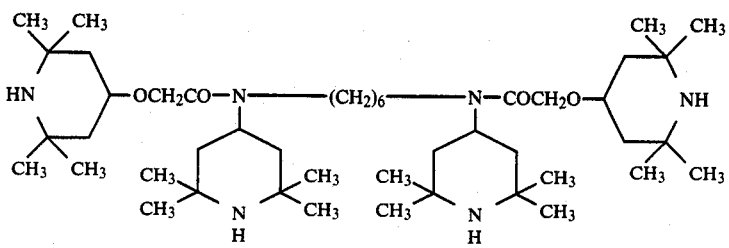

according to claim 1.
6. The compound of the formula:

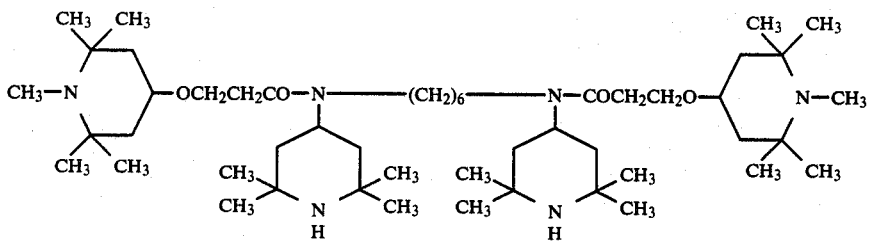

according to claim 1.
7. The compound of the formula:

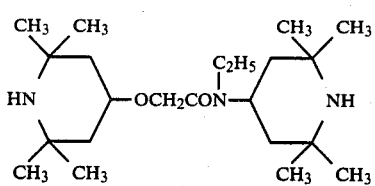

according to claim 1.
8. The compound of the formula:

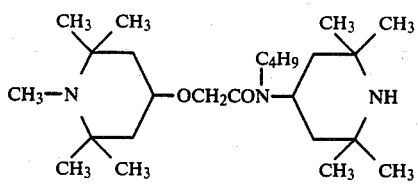

according to claim 1.
9. A light-stabilised, heat-stabilised and oxidation-stabilised polymer composition comprising a synthetic polymer and one or more stabilisers of the formula (I) in a quantity from 0.01 to 5% by weight relative to the weight of the synthetic polymer.

10. A composition according to claim 9, which, in addition to the novel stabiliser, also comprises other conventional additives for synthetic polymers.

11. A composition according to claim 9, wherein the synthetic polymer is polypropylene or polyethylene.

12. A composition according to claim 9, comprising a synthetic polymer and as a stabilizer of formula I a compound of the formula

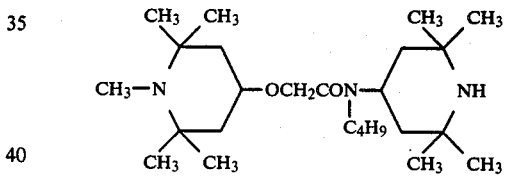

13. A composition according to claim 9, comprising a synthetic polymer and as a stabilizer of formula I a compound of the formula

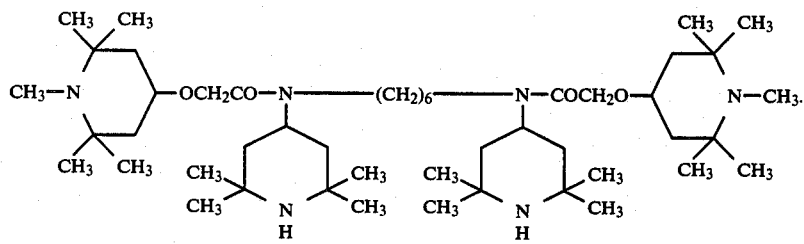

14. A composition according to claim 9 wherein the quantity of the stabilizers by weight relative to the weight of the synthetic polymer is from 0.05 to 1% by weight.

* * * * *